(12) United States Patent
Friedrich et al.

(10) Patent No.: US 7,019,164 B2
(45) Date of Patent: *Mar. 28, 2006

(54) PROCESS FOR THE PRODUCTION OF (POLY)ISOCYANATES IN THE GAS PHASE

(75) Inventors: Martin Friedrich, Köln (DE); Herbert Stutz, Dormagen (DE)

(73) Assignee: Bayer Aktiengesellschaft, Leverkusen (DE)

(*) Notice: Subject to any disclaimer, the term of this patent is extended or adjusted under 35 U.S.C. 154(b) by 57 days.

This patent is subject to a terminal disclaimer.

(21) Appl. No.: 10/316,749

(22) Filed: Dec. 11, 2002

(65) Prior Publication Data

US 2003/0114705 A1 Jun. 19, 2003

(30) Foreign Application Priority Data

Dec. 14, 2001 (DE) .............................. 101 61 384

(51) Int. Cl.
*C07C 253/00* (2006.01)
(52) U.S. Cl. ..................................... 560/347; 560/336
(58) Field of Classification Search ................ 560/330, 560/336, 338, 355
See application file for complete search history.

(56) References Cited

U.S. PATENT DOCUMENTS

| | | | |
|---|---|---|---|
| 4,847,408 A | 7/1989 | Frosch et al. | 560/347 |
| 5,391,683 A | 2/1995 | Joulak et al. | 528/67 |
| 5,449,818 A | 9/1995 | Biskup et al. | 560/347 |
| 5,516,935 A | 5/1996 | Bischof et al. | 560/347 |
| 5,633,396 A | 5/1997 | Bischof et al. | 560/347 |
| 6,100,326 A * | 8/2000 | Richter et al. | 524/591 |
| 2003/0069441 A1* | 4/2003 | Leimkuhler et al. | 560/347 |

* cited by examiner

*Primary Examiner*—Johann Richter
*Assistant Examiner*—Karl Puttlitz
(74) *Attorney, Agent, or Firm*—Joseph C. Gil; Thomas W. Roy

(57) ABSTRACT

The present invention relates to a process for the production of an isocyanate corresponding to the formula $R(NCO)_n$ wherein R represents a (cyclo)aliphatic or aromatic hydrocarbon residue having up to 15 carbon atoms, preferably 4 to 13 carbon atoms, provided that there are at least 2 carbon atoms arranged between each of the nitrogens and n represents the number 2 or 3, by a) separately heating an amine corresponding to the formula $R(NH_2)_n$, wherein R and n are as previously defined, in vapor form, optionally diluted with an inert gas or the vapors of an inert solvent, and phosgene to temperatures of 200° C. to 600° C., b) continuously reacting the optionally diluted amine and phosgene in a reactor which has a reaction chamber that does not have moving parts, wherein the reactor has a diameter D and centrally located in the reactor is a nozzle having an orifice diameter d, i) by introducing the optionally diluted amine into the reactor through the nozzle and by introducing phosgene through the annular space around the nozzle such that the amine and phosgene flow in parallel through the reactor and ii) mixing and reacting the amine and phosgene to form the isocyanate of formula I) by introducing the amine through the orifice into a stream of phosgene in the reaction chamber, wherein the gas velocity of the optionally diluted amine is higher than the gas velocity of phosgene and the ratio of the narrower nozzle diameter d to the reactor diameter D is from 5% to 45%.

5 Claims, 1 Drawing Sheet

PROCESS FOR THE PRODUCTION OF (POLY)ISOCYANATES IN THE GAS PHASE

FIELD OF THE INVENTION

The present invention relates to an improved process for the production of (poly)isocyanates in the gas phase with optimized mixing of the reactants.

BACKGROUND OF THE INVENTION

It is known that good mixing of the reactants plays an important role in gas phase reactions in achieving elevated conversions and selectivities. Examples are the gas phase phosgenation of aromatic or (cyclo)aliphatic polyfunctional amines. In a continuous process the educts are conventionally introduced into a reactor in gaseous form, as described in various patent applications (for example EP-A 676 392, EP-A 570 799, EP-A 289 840, EP-A 749 958). Mixing of the reaction partners to a degree of segregation of $10^{-3}$ should proceed within a period of up to 0.5 seconds. The degree of segregation is a measure of the incompleteness of mixing (EP-A 570 799).

Methods for achieving short mixing times are known in principle. Mixing units having moving or static mixing elements are suitable. Static mixing elements are preferred. A range of different possible embodiments is conceivable for the design of static mixing elements, for example using nozzles, flat jet nozzles or venturi nozzles known from combustion technology.

Disadvantages of many designs are elevated pressure loss or an arrangement which results in insufficiently rapid mixing or backmixing in the mixing zone itself or in the reaction chamber. Elevated pressure loss in the mixing element entails increased effort in the preparation of the gaseous educts. A higher pressure is also associated with an increased boiling temperature. This may result in thermal damage to educts on vaporization and in the formation of secondary products.

Insufficiently rapid mixing or backmixing may result in an increased residence time of a proportion of the educts and products, resulting in unwanted parallel or subsequent reactions. Under certain circumstances, another consequence of inadequate mixing is a non-uniform temperature distribution in the reactor. As a consequence, there may be zones in the reactor which are excessively hot, resulting in increased thermal decomposition of the products. Decomposition products form a solid residue, which is deposited on the reactor wall. In this case, it is conventional to provide the reactor with an inliner which, once encrusted, can be exchanged, substantially facilitating reactor cleaning.

It is an object of the present invention to overcome the preceding disadvantages of known processes for the gas phase phosgenation of amines.

This object may be achieved according to the process of the present invention. It has been found that the known disadvantages may be minimized if the mixing element used is a nozzle with precisely specified dimensions which is incorporated coaxially into a tube which opens directly into the reaction chamber as described hereinafter.

SUMMARY OF THE INVENTION

The present invention relates to a process for the production of an isocyanate corresponding to formula I)

$$R(NCO)_n \qquad (I),$$

wherein
R represents a (cyclo)aliphatic or aromatic hydrocarbon residue having up to 15 carbon atoms, preferably 4 to 13 carbon atoms, provided that there are at least 2 carbon atoms arranged between each of the nitrogens and
n represents the number 2 or 3, by
a) separately heating an amine corresponding to formula II)

$$R(NH_2)_n \qquad (II),$$

wherein R and n are as previously defined, in vapor form, optionally diluted with an inert gas or the vapors of an inert solvent, and phosgene to temperatures of 200° C. to 600° C.,
b) continuously reacting the optionally diluted amine and phosgene in a reactor which has a reaction chamber that does not have moving parts, wherein the reactor has a diameter D and centrally located in the reactor is a nozzle having an orifice diameter d,
  i) by introducing the optionally diluted amine into the reactor through the nozzle and by introducing phosgene through the annular space around the nozzle such that the amine and phosgene flow in parallel through the reactor and
  ii) mixing and reacting the amine and phosgene to form the isocyanate of formula I) by introducing the amine through the orifice into a stream of phosgene in the reaction chamber, wherein the gas velocity of the optionally diluted amine is higher than the gas velocity of phosgene and the ratio of the narrower nozzle diameter d to the reactor diameter D is from 5% to 45%.

BRIEF DESCRIPTION OF THE DRAWING

The FIGURE represents a preferred embodiment of the reactor used in the process of the present invention.

DETAILED DESCRIPTION OF THE INVENTION

Figure 1:
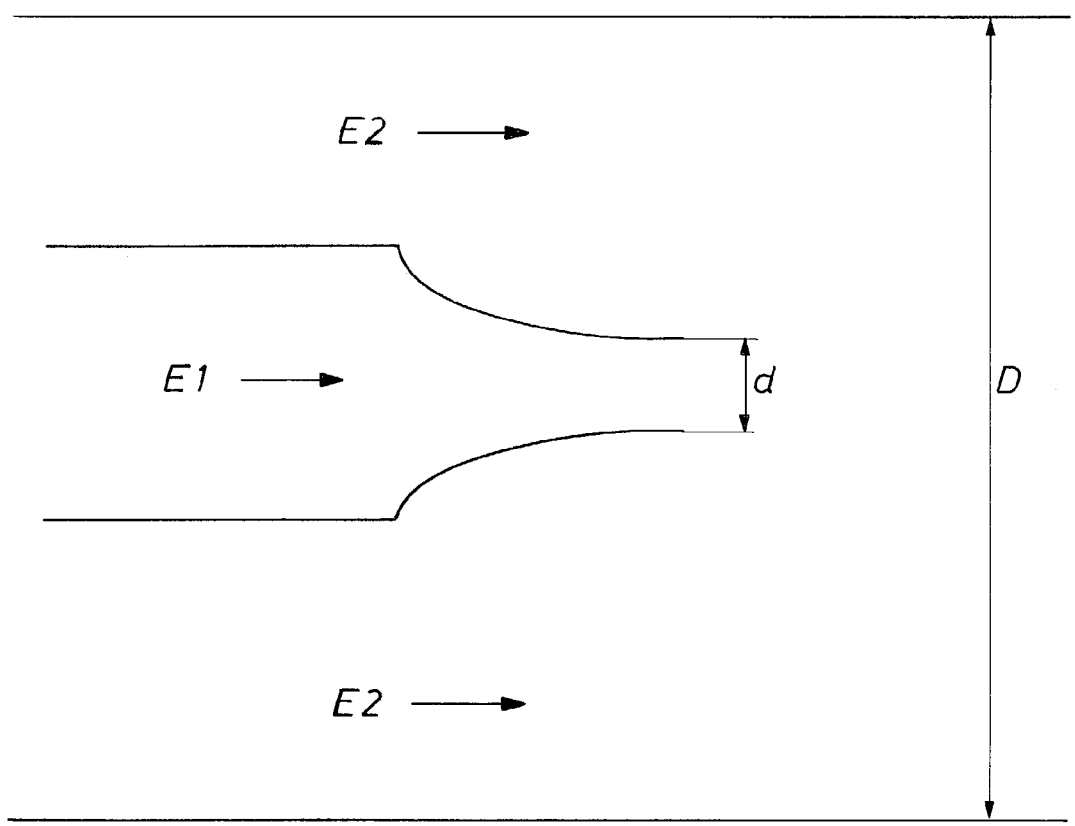

Mixing of the vaporous reactants proceeds immediately downstream from the nozzle outlet. The FIGURE shows a mixing element with nozzle according to the invention. In these mixing elements, the arrangement is such that two gaseous educts are reacted and flow in parallel through a reactor of diameter D. In this case, an amine E1 is introduced via a nozzle with an orifice diameter d centrally into a stream of phosgene E2, wherein the gas velocity of E1 is high relative to the gas velocity of E2.

It has been found that there is a specific geometry of mixing element and reactor, a nozzle arrangement with a certain ratio of diameters d/D, at which the influences arising from pressure loss in the stream of injected educt and quality of mixing in the reaction zone permit optimum reactor operation. It has been found for the gas phase reaction of amines with phosgene to yield isocyanates in the process according to the invention, it is particularly advantageous to feed amine centrally into a stream of phosgene via a nozzle, the smallest diameter of which is 5 to 45%, preferably 10 to 25%, of the reactor diameter.

In the process according to the invention, diisocyanates and/or triisocyanates are produced from the corresponding diamines and/or triamines.

The diisocyanates produced in the process according to the invention are preferably those of formula III)

$$ONC-R-NCO \quad (III),$$

wherein

R has the meaning stated in formula I),

The diisocyanates are prepared by phosgenating diamines, preferably of the formula IV)

$$H_2N-R-NH_2 \quad (IV),$$

wherein

R has the meaning stated in formula I).

The preferred triisocyanate of formula I is 1,8-diisocyanato-4-(isocyanatomethyl)octane (triisocyanatononane or TIN).

Typical examples of suitable aliphatic diamines are described, for example, in EP-A 0 289 840 (believed to correspond to U.S. Pat. No. 4,847,408, herein incorporated by reference). Suitable aliphatic triamines are described, for example, in EP-A 749 958 (believed to correspond to U.S. Pat. No. 5,633,396, herein incorporated by reference). Isophorone diamine (IPDA), hexamethylene diamine (HDA) and bis(4-aminocyclohexyl)methane are preferred.

Examples of suitable aromatic diamines include the pure isomers or the isomer mixtures of diaminobenzene, diaminotoluene, diaminodimethylbenzene, diaminonaphthalene and diaminodiphenylmethane. Mixtures of 2,4- and 2,6-tolylene diamine having 80/20 and 65/35 isomer ratios by weight and the pure 2,4-tolylene diamine isomer are preferred.

Before the process according to the invention is performed, the starting amines of the formula II) are vaporized and heated to 200° C. to 600° C., preferably to 250° C. to 450° C., optionally diluted with inert gas (such as Ne, He, Ar or with the vapors of an inert solvent), and introduced into the reactor.

Prior to being introduced into the reactor of diameter D, the phosgene used in the phosgenation reaction is heated to a temperature of 200° C. to 600° C., preferably of 250° C. to 450° C.

The FIGURE represents a preferred embodiment of the present invention. The two gaseous educts flow in parallel through a reactor of diameter D. Amine E1 is introduced centrally via a nozzle with an orifice diameter d into a stream of phosgene E2. The gas velocity of E1 is higher than the gas velocity of E2. In the process according to the invention, the amine flows through the nozzle, while phosgene is passed through the annular space around the nozzle. The ratio of the narrowest nozzle diameter d to reactor diameter D is preferably 5% to 45%, more preferably 10% to 25%.

During the process according to the invention, the pressure in the feed lines to the reaction chamber is preferably 200 mbar to 3000 mbar and the pressure at the outlet from the reaction chamber is preferably 150 mbar to 2000 mbar. The flow velocity within the reaction chamber, which is at least 3 m/s, preferably of at least 6 m/s and more preferably 10 m/s to 120 m/s, is ensured by maintaining a suitable pressure differential. Under these conditions, turbulent flow generally prevails within the reaction chamber.

The advantages of the process according to the invention are:

(a) a uniform reaction zone avoiding hot spots,
(b) slight formation of secondary products and
(c) avoidance of solid deposits on the reactor wall The invention is further illustrated but is not intended to be limited by the following examples in which all parts and percentages are by weight unless otherwise specified.

EXAMPLE

Example 1

Isophorone diamine (IPDA), phosgene and nitrogen flowed continuously in a molar ratio of 1:4:0.1 into a mixing tube with a downstream diisocyanate condensation stage (and subsequent isocyanate processing) through a nozzle which projected into the mixing tube (see the FIGURE). The educts were vaporized separately from one another in upstream heat exchangers and adjusted to a temperature of 320° C. A mixture of nitrogen and IPDA (E1) flowed through the nozzle, while phosgene (E2) flowed through the annular space around the nozzle. The ratio of the diameters of nozzle (d) and reaction chamber (D) was 0.18:1. The pressure in the reaction zone was slightly above atmospheric pressure. The flow velocity of the reaction mixture downstream from the nozzle was approx. 20 m/s. After leaving the reactor, the reaction product isophorone diisocyanate (IPDI) was condensed and separated from excess phosgene and the secondary product, hydrogen chloride, and sent for purification. The yield of IPDI relative to the IPDA that was introduced was 98.8% of theoretical. The selected arrangement permitted highly uniform operation. After operation for two weeks, the reactor exhibited no appreciable soiling.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of an isocyanate corresponding to formula I)

$$R(NCO)_n \quad (I),$$

wherein

R represents a (cyclo)aliphatic or aromatic hydrocarbon residue having up to 15 carbon atoms, provided that there are at least 2 carbon atoms arranged between each of the nitrogens in the (NCO) of formula 1 and n represents the number 2 or 3, which comprises a) separately heating amines corresponding to formula II)

$$R(NH_2)_n \quad (II),$$

wherein R and n are as previously defined, in vapor form, optionally diluted with an inert gas or the vapors of an inert solvent, and phosgene to temperatures of 200° C. to 600° C., b) continuously reacting the optionally diluted amine and phosgene in a reactor which has a reaction chamber that does not have moving parts, wherein the reactor has a diameter D and centrally located in the reactor is a nozzle having an orifice diameter d, i) by introducing the optionally diluted amine into the reactor through the nozzle and by introducing phosgene through the annular space around the nozzle such that the amine and phosgene flow in parallel through the reactor and ii) mixing and reacting the amine and phosgene to form the isocyanate of formula I) by introducing the amine through the orifice into a stream of phosgene in the reaction chamber, wherein the gas velocity of the optionally diluted amine is higher than the gas velocity of phosgene and the ratio of the narrower nozzle diameter d to the reactor diameter D is from 10% to 25%.

2. The process of claim 1 wherein n is 2.

3. The process of claim 1 wherein the amines in a) are isophorone diamine, hexamethylene diamine or bis(4-aminocyclohexyl)methane.

4. The process of claim 1 wherein the amines in a) are 2,4-tolylene diamine or a mixture of 2,4- and 2,6-tolylene diamine at an 80/20 or 65/35 isomer ratio by weight.

5. The process of claim 1 wherein the isocyanates of formula (I) are triisocyanatononane.

* * * * *